United States Patent [19]
Farris et al.

[11] Patent Number: 4,822,603
[45] Date of Patent: Apr. 18, 1989

[54] ANTIPERSPIRANT STICK COMPOSITION AND PROCESS FOR PREPARING THE SAME

[75] Inventors: Richard D. Farris, Cincinnati, Ohio; John P. Luebbe, Lawrenceburg, Ind.; Gerald J. Quinlivan, Cincinnati, Ohio

[73] Assignee: The Procter & Gamble Company, Cincinnati, Ohio

[21] Appl. No.: 55,488

[22] Filed: May 28, 1987

Related U.S. Application Data

[63] Continuation-in-part of Ser. No. 875,901, Jun. 18, 1986, abandoned.

[51] Int. Cl.⁴ .......................... A61K 7/32; A61K 7/34; A61K 7/36; A61K 7/38
[52] U.S. Cl. .............................. 424/66; 424/DIG. 5; 424/67; 424/68
[58] Field of Search ..................... 424/DIG. 5, 68, 66

[56] References Cited

U.S. PATENT DOCUMENTS

| | | | |
|---|---|---|---|
| 4,049,792 | 9/1977 | Elsnau | 424/66 |
| 4,053,581 | 10/1977 | Pader et al. | 424/63 |
| 4,126,679 | 11/1978 | Davy et al. | 424/66 |
| 4,147,766 | 4/1979 | Kozischek | 424/14 |
| 4,229,432 | 10/1980 | Geria | 424/68 |
| 4,265,878 | 5/1981 | Keil | 424/DIG. 5 |
| 4,268,499 | 5/1981 | Keil | 424/68 |
| 4,280,994 | 7/1981 | Turney | 424/68 |
| 4,379,136 | 4/1983 | Machida | 424/DIG. 5 |
| 4,574,082 | 3/1986 | Tietjen et al. | 424/63 |
| 4,659,564 | 4/1987 | Cox et al. | 424/DIG. 5 |

FOREIGN PATENT DOCUMENTS

| | | | |
|---|---|---|---|
| 117070 | 8/1984 | European Pat. Off. | 424/66 |
| 120210 | 10/1984 | European Pat. Off. | 424/68 |
| 2018590 | 10/1979 | United Kingdom | 424/47 |
| 2139496 | 11/1984 | United Kingdom | 424/68 |

OTHER PUBLICATIONS

J. Hardy, et al., "The Use of Fumed Silica in Cosmetics" 2 Cosmetic Technology 35 (1980).
C. Fox, "Gels and Sticks, Review and Update", 99 Cosmetics and Toiletries 19–52 (1984).
N. Geria, "Formulation of Stick Antiperspirants and Deodorants" 99 Cosmetics & Toiletries 55–66 (1984).
Cosmetics and Toiletries, 12/1985, vol. 100, pp. 68–73 and 75.

Primary Examiner—Dale R. Ore
Attorney, Agent, or Firm—David L. Suter; Steven J. Goldstein; Kim William Zerby

[57] ABSTRACT

Antiperspirant stick compositions comprising:
- (a) from about 35% to about 60% of a volatile silicone oil;
- (b) from about 1% to about 5% of a non-volatile emollient;
- (c) from about 2.5% to about 4% of a high melting point wax;
- (d) from about 10% to about 15% of a low melting point wax;
- (e) from about 0.2% to about 1.5% of a colloidal silica material;
- (f) from about 0.5% to about 4% of an inert spherical particulate material which is comprised of essentially spherical particles having a mean diameter of at least about 10 microns;
- (g) from about 2% to about 9% of a talcum material; and
- (h) from about 20% to about 33% of a particulate antiperspirant material;

wherein the total level of talcum material and antiperspirant material is from about 25% to about 35%.

16 Claims, No Drawings

ANTIPERSPIRANT STICK COMPOSITION AND PROCESS FOR PREPARING THE SAME

CROSS REFERENCE TO RELATED APPLICATION

This is a continuation-in-part application of copending application Ser. No. 875,901, filed June 18, 1986, now abandoned.

BACKGROUND OF THE INVENTION

The present invention relates to antiperspirant compositions suitable for use in solid stick form. More particularly, it relates to such antiperspirants with improved cosmetic characteristics.

Many solid antiperspirant compositions are described in the chemical and cosmetic literature. In general, there are three types of such antiperspirant stock formulations: compressed powder sticks, gel sticks and wax sticks. While each of these formulation types may have advantages in certain situations, each also has disadvantages. For example, compressed powder sticks are often brittle and hard, and leave a cosmetically-unacceptable dust upon application. Gels may be unstable due to evaporation of alcohol and (more importantly) due to interaction of astringent metal salts with the soaps used in the sticks. Wax-based formulations can also yield cosmetically-unacceptable products due to such factors as hardness, greasiness and stickiness. Nevertheless, the increased stability and antiperspirant efficacy afforded by wax-based formulations has resulted in such sticks being generally preferred for antiperspirant stick products.

The use of a wide variety of materials is described in the literature in order to optimize the cosmetic characteristics of antiperspirant wax-based sticks. For example, U.S. Pat. No. 4,126,679, Davy, et al., issued Nov. 21, 1978, describes antiperspirant sticks containing volatile silicone oils, long-chain fatty alcohols, and a powdered material (such as an antiperspirant active, fumed silica, talc or sodium bicarbonate) for stable sticks with good glide properties. U.S. Pat. No. 4,280,994, Turney, issued July 28, 1981, claims antiperspirant sticks containing volatile silicone, a waxy material and polyethylene glycol, in order to ease application of the composition. British Patent Application No. 2,139,496, Geria, published Nov. 14, 1984, describes the use of a water-soluble emollient in order to avoid the waxy feel of a wax-based antiperspirant stick. European Patent Publication No. 117,070, May, published Aug. 29, 1984, describes wax-based antiperspirant sticks containing certain fatty alcohols in order to increase product stability.

While many stick formulations described in the literature may have certain desirable characteristics, such as acceptable product hardness and stability, or pleasing aesthetics or application characteristics, or good in-use characteristics. Few, if any, sticks provide good performance in all respects. For example, sticks that have good "glide" or other good application characteristics may, however, have poor stability and may be too soft. Such sticks typically also produce undesirable sensations of stickiness on the skin, after application. Conversely, sticks which are dimensionally stable and of adequate hardness may impart a waxy feel and have poor application characteristics. Furthermore, the wax-based sticks described in the literature typically produce high levels of visible residue which is aesthetically unappealing and may leave visible soil on clothing.

It has now been discovered that wax-based antiperspirant sticks containing selected emollients, fillers, and waxes provide good overall cosmetics, both during application to the skin, as well as in-use after application. In particular, the compositions of the present invention afford dry, non-sticky, non-waxy in-use characteristics, with low levels of visible residue, combined with good "glide" and other desirable application characteristics. The sticks of this invention also have good product stability and hardness.

SUMMARY OF THE INVENTION

The present invention provides antiperspirant compositions comprising:
 (a) from about 35% to about 60% of a volatile silicone oil;
 (b) from about 1% to about 5% of a non-volatile emollient;
 (c) from about 2.5% to about 4% of a high melting point wax;
 (d) from about 10% to about 15% of a low melting point wax;
 (e) from about 0.2% to about 1.5% of a colloidal silica material;
 (f) from about 0.5% to about 4% of an inert spherical particulate material with which is comprised of essentially spherical particulates having a mean diameter of at least about 10 microns;
 (g) from about 2% to about 9% of a talcum material; and
 (h) from about 20% to about 33% of a particulate antiperspirant material;
wherein the total level of said talcum material and said antiperspirant material is from about 25% to about 35%.

DESCRIPTION OF THE INVENTION

The antiperspirant compositions of this invention contain eight essential ingredients: a volatile silicone oil, a non-volatile emollient, a high melting point wax, a low melting point wax, a colloidal silica material, an inert spherical particulate material, a talcum material, and an antiperspirant active. These compositions (herein "antiperspirant compositions") encompass any solid (or semi-solid) composition intended for human use in order to deposit antiperspirant material on human tissue. The present compositions may be produced in a solid stick form, suitable for application using a conventional stick dispenser. The essential and optional components to be included in the present antiperspirant compositions must be "cosmetically-acceptable", i.e., safe for human use and aesthetically acceptable as the levels at which such materials are used in the present compositions, at a reasonable risk/benefit ratio.

Specifically, the antiperspirant compositions of the present invention comprise:
 (a) from about 35% to about 60% of a volatile silicone oil;
 (b) from about 1% to about 5% of a non-volatile emollient;
 (c) from about 2.5% to about 4% of a high melting point wax;
 (d) from about 10% to about 15% of a low melting point wax;
 (e) from about 0.2% to about 1.5% of a colloidal silica material;

(f) from about 0.5% to about 4% of an inert spherical particulate material with which is comprised of essentially spherical particulates having a mean diameter of at least about 10 microns;

(g) from about 2% to about 9% of a talcum material; and (h) from about 20% to about 33% of a particulate antiperspirant material;

wherein the total level of said talcum material and said antiperspirant material is from about 25% to about 35%. (All percentages herein are by weight of total composition.)

Preferably, the present antiperspirant sticks contain from about 45% to about 55% of the volatile silicone oils. The nonvolatile emollients are preferably present at a level of from about 2.0% to about 4.0%, more preferably from about 2.5% to about 3.5%. The high melting point wax is preferably present at a level of from about 2.5% to about 3.5%, and the low melting point wax preferably present at a level of from about 10.5% to about 13%. Preferably, the colloidal silica material is present at a level of from about 0.4% to about 1.0%, more preferably from about 0.4% to about 0.8%. The inert spherical particulate material is preferably present at a level of from about 0.5% to about 1.5%. The total level of antiperspirant material and talcum material is preferably from about 28% to about 33%. For compositions containing from about 25% to about 28% antiperspirant active material, the talcum material is preferably present at a level of from about 2.5 to about 5.5%, more preferably from about 3% to about 5%. Also in such compositions, the total level of the inert spherical particulate material and the talcum material is preferably less than about 7%, more preferably less than about 6%. Also preferably, the present compositions are substantially anhydrous, i.e., containing less than about 2% of free (chemically unbound) water.

Essential Components

Volatile Silicone Oil:

The antiperspirant compositions of this invention contain a volatile polyorganosiloxane, which may function as a liquid emollient. (As used herein, "volatile" refers to those materials which have a measurable vapor pressure at ambient conditions.) The volatile polyorganosiloxanes useful herein may be cyclic or linear. A description of various volatile silicones is found in Todd, et al., "Volatile Silicone Fluids for Cosmetics", 91 *Cosmetics and Toiletries* 27–32 (1976), incorporated by reference herein. Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 345, and Dow Corning 200 (manufactured by the Dow Corning Corporation); Silicone 7207 and Silicone 7158 (manufactured by the Union Carbide Corporation); SF1202 (manufactured by General Electric); and SWS-03314 (manufactured by Stouffer Chemical).

Non-volatile Emollient:

The present antiperspirant compositions contain one or more non-volatile emollients. Such materials include fatty acid and fatty alcohol esters, water-insoluble ethers and alcohols, polyorganosiloxanes, and mixtures thereof. Emollients among those useful herein are described in 1 *Cosmetics, Science and Technology* 27–104 (M. Balsam and E. Sagarin ed. 1972), and U.S. Pat. No. 4,202,879, Shelton, issued May 13, 1980 (both incorporated by reference herein).

The present compositions preferably contain a nonvolatile silicone oil as an emollient material. Such silicone oils include polyalkylsiloxanes, polyalkyarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present composition are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicon surfactant (sold by General Electric Company). Polysiloxane ethylene glycol ether copolymers are preferred copolymers for use in the present compositions.

High Melting Point Wax:

The antiperspirant compositions of the present invention contain one or more materials having wax-like characteristics and having a melting point of from about 65° C. to about 102° C. Such waxes include beeswax, spermaceti, carnauba, baysberry, candelilla, montan, ozokerite, ceresin, paraffin, hydrogenated castor oil (castor wax), synthetic waxes such as Fisher-Tropsch waxes, microcrystalline wax, and mixtures thereof. Castor wax is a preferred high-melting point wax useful herein. Such high-melting point waxes among those useful herein are disclosed in U.S. Pat. No. 4,049,792, Elsnau, issued Sept. 20, 1977 (incorporated by reference herein.)

Low Melting Point Wax:

The present antiperspirant compositions also contain wax-like materials having a low melting point, i.e., having a melting point of from about 37° C. to about 75° C. Such materials include fatty acids, fatty alcohols, fatty acids esters and fatty acid amides, having fatty chains of from about 8 to about 30 carbon atoms, preferably from about 12 to about 18 carbon atoms, and mixtures thereof. Preferred low melting point waxes include cetyl alcohol, palmitic acid, myristyl alcohol, stearyl alcohol, paraffin, and mixtures thereof. Stearyl alcohol, cetyl alcohol, and mixtures thereof are particularly preferred.

Colloidal Silica Material:

The present antiperspirant sticks contain a finely divided silica material, herein a "colloidal silica material", which is comprised of micron to sub-micron sized silica particulates, with high surface areas (preferably greater than about 100 square meters per gram of material). Preferably, the colloidal silica material is less than about 1 micron in size. Also preferably, the silica material used in the present compositions is a fumed silica. Fumed silicas can generally be described as fluffy, white, superfine powders of extremely low bulk density but having high surface areas. These fumed silicas are typically made by a vapor phase process that produces colloidal silica by the hydrolysis of silicon tetrachloride at a very high temperature. These materials typically consist of about 99.8% silicon dioxide by weight (on a moisture free basis), existing in three dimensional branched chain aggregates, with a surface that is hydrophilic and capable of hydrogen bonding. Such silicas have surface areas ranging from about 2.5 to about 1,200 square meters per gram. Colloidal silica materials are described in Hardy, et al., "The Use of Fumed Silica in Cosmetics", 2 *Cosmetic Technology* 35 (1980) (incorporated by reference herein) and R. Iler, *The Chemistry of Silica* (1979).

Colloidal silica materials among those useful herein are available from a variety of sources, including Syloid silicas (manufactured by Davison Chemical Division of W. R. Grace), Cab-O-Sil (manufactured by Cabot Corporation), and Aerosil (manufactured by Degussa A.G.). Cab-O-Sil is a particularly preferred commercially available colloidal silica useful herein, with a surface area ranging from about 200 to about 400 square meters per gram.

Inert Spherical Particulate Material:

The antiperspirant compositions of this invention also contain an "inert spherical particulate material" comprising essentially-spherical particulates having a mean diameter of at least about 10 microns. Preferably, the inert spherical particulate material is essentially free of (i.e., containing less than 2% by weight of material) particulates having diameters greater than about 150 microns. Also preferably, the particles have a mean diameter of from about 15 microns to about 75 microns. Commercially-available inert particulate materials among those useful herein may be of a non-uniform size distribution, containing some particles outside the size ranges described herein. For the purposes of this invention, such non-uniform materials preferably have a mean diameter within the ranges described above.

As referred to herein, "inert particulates" are those particulates comprised of materials or mixtures of materials that are essentially water insoluble and which neither melt nor decompose nor react with the wax materials, silicone oils or other components of the antiperspirant sticks, under the conditions of preparation and of use. Among the particulate materials that may be incorporated in this invention include those comprised of polyolefins (such as polystyrene, polyethylene, and polypropylene), nylon, Teflon ®, insoluble cross-linked starches, and mixtures thereof.

Preferred inert particulate materials include those comprised of polyolefins, particularly polyethylene. Polyethylene materials, as well as particulates made from other polyolefins, can be prepared by any of several methods known in the art. (See, e.g., U.S. Pat. No. 2,825,721, Hogan, et al., issued Mar. 4, 1958.) Polyethylene polymers with low molecular weights of 1,500 to 3,000, as well as polymers of such high molecular weights as 35,000 to 100,000, may be used. One such polyethylene powder useful in this invention is Microthene ®, manufactured by U.S.I. Chemicals, having a mean particle diameter of from about 14 to about 20 microns. Among other commercially-available materials useful herein are 3M Glass Bubbles (soda-lime borosilicate glass spheres sold by 3M Company) and Miralite (low density polyvinylidene chloride hollow microspheres, of approximately 30 microns mean diameter, sold by Pierce & Stevens Chemical Corporation).

Talcum Material:

In addition to the inert spherical particulate material and the colloidal silica material, the antiperspirant compositions of this invention also contain talc or a talc-like material, herein a "talcum material", which is an inert, soft, impalpable powder. Talc is described in K. S. Plotkin, "Cosmetic Talc" 11 *C.T.F.A. Cosmetic Journal* 13–16 (1979), incorporated by reference herein. Among talcum materials useful herein are silicate powders (including talc, aluminum silicate, and magnesium silicate), modified corn starches, metallic stearates, and mixtures thereof. Such commercially-available materials include Veecote (anhydrous aluminum silicate, sold by R. T. Vanderbilt Company, Inc.) and Dry Flo (aluminum starch succinate, sold by National Starch and Chemicals Company).

Particulate Antiperspirant Material:

The particulate antiperspirant materials of this invention comprise any compound or composition having antiperspirant activity. Astringent metallic salts are preferred antiperspirant material for use herein, particularly including the inorganic and organic salts of aluminum, zirconium and zinc, and mixtures thereof. Particularly preferred are the aluminum and zirconium salts such as aluminum halides, aluminum hydroxide halides, zirconyl oxide halides, zirconyl hydroxy halides, and mixtures thereof.

Preferred aluminum salts include those of the formula

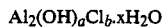

$$Al_2(OH)_aCl_b \cdot xH_2O$$

wherein a is from about 2 to about 5; $a+b=6$; x is from about 1 to about 6; and wherein a, b, and x may have non-integer values. Particularly preferred are aluminum chlorhydroxides referred to as $=5/6$ basic chlorhydroxide", wherein $a=5$, and "⅔ basic chlorhydroxide," wherein $a=4$. Processes for preparing aluminum salts are disclosed in the following documents, all incorporated by reference herein: U.S. Pat. No. 3,887,692, Gilman, issued June 3, 1975; U.S. Pat. No. 3,904,741, Jones et al., issued Sept. 9, 1975; U.S. Pat. No. 4,359,456, Gosling, et al., issued Nov. 16, 1982; and British Patent Specification No. 2,048,229, Fitzgerald, et al., published Dec. 10, 1980. Mixtures of aluminum salts are described in British Patent Specification No. 1,347,950, Shin, et al., published Feb. 27, 1974 (incorporated by reference herein).

Zirconium salts are also preferred for use in antiperspirant sticks of the present invention. Such salts are of the general formula

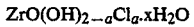

$$ZrO(OH)_{2-a}Cl_a \cdot xH_2O$$

wherein a is from about 1.5 to about 1.87; x is from about 1 to about 7; and wherein a and n may have non-integer values. These zirconium salts are disclosed in Belgium Pat. No. 825,146, Schmitz, issued Aug. 4, 1975, (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in U.S. Pat. No. 3,679,068, Luedders, et al., issued Feb. 12, 1974 (incorporated herein by reference), and U.S. Pat. No. 4,120,948, Shelton, issued Oct. 17, 1978 (incorporated by reference herein).

Non-essential Components

The compositions of the present invention may also contain optional components which modify the physical characteristics of the vehicles, or serve as "active" components when deposited on the skin in addition to the particulate antiperspirant material. Additional active components include bacteriostats and fungistats. The particular non-active components that may be useful will depend upon the form of application that is desired. Such components include, for example, emollients, colorants, perfumes, nd emulsifiers. Optional components useful herein are described in the following documents, all incorporated by reference herein: U.S. Pat. No. 4,049,792, Elsnau, issued Sept. 20, 1977; Canadian Pat. No. 1,164,347, Beckmeyer, et al., issued Mar. 27, 1984; European Patent Specification No. 117,070, May, published Aug. 29, 1984; and Geria, "Formulation of Stick Antiperspirants and Deodorants," 99 *Cosmetics & Toiletries* 55–60 (1984).

One preferred optional component is a "long-chain fatty alcohol" (i.e., one or more fatty alcohols, each having a chain of twenty or more carbon atoms) to maintain proper hardness and strength of the stick compositions. Eicosanol, or eicosyl ($C_{20}$) alcohol, is a preferred long-chain fatty alcohol. Preferably, the long-chain fatty alcohol is incorporated at a level such that the total of such long-chain fatty alcohols present in the stick composition (including the long-chain fatty alcohols that are naturally present along with the low melting point wax) is from about 1% to about 3%, preferably from about 1% to about 2% (by total weight of fatty alcohol in the composition). The use of such long-chain fatty alcohols in antiperspirant sticks is described in European Patent Specification No. 117,020, May, published Aug. 29, 1984 (incorporated by reference herein).

The antiperspirant compositions of this invention that are to be made in stick form may be produced using methods among those known in the art. Such processes include those generally comprising the steps of:

(a) admixing the essential and optional composition materials at a temperature sufficient to melt the waxes and dissolve them in the silicone materials;

(b) pouring the composition into stick-form molds, and (c) cooling to form a solid stick composition.

Typically, the wax materials and silicone materials are admixed at a temperature of from about 70° C. to about 95° C. (depending upon the type and level of waxes and other composition components). The bulk composition is typically cooled to a temperature of from about 55° C. to about 60° C. prior to pouring into stick-form molds.

Care should be taken in the processes of making these compositions so as to maintain uniform distribution of particulate materials throughout the antiperspirant sticks. Specific essential and non-essential materials to be included, and their levels, are selected in order to produce a stick of desired hardness, so as to maintain dimensional stability while depositing a suitable amount of antiperspirant material on the skin during normal use. Hardness of sticks can be determined by a variety of methods, including American Society for Testing and Materials (ASTM) Method D-5. This method involves the use of a needle of particular weight and dimension, which is allowed to travel downward through the stick material for a pre-determined period of time. The distance traveled by the needle is a relative measure of the stick hardness. Utilizing Method D-5, with a #1554 penetration needle (manufactured by Sergeant-Welch Scientific Company) weighing 50 grams, and a Precision Model 73515 Penetrometer (manufactured by Precision Scientific, subsidiary of GCA Corporation), the antiperspirant sticks of the present invention preferably yield a penetration of from about 60 to about 150 millimeters, more preferably from about 70 to about 130 millimeters, over a period of 5 seconds.

It has been found that, in the processes for making antiperspirant sticks described above, if the temperature of the composition is carefully controlled prior to pouring the composition into stick-form molds, then preferred compositions of this invention may be produced. Such preferred sticks have a matrix comprised of small, randomly-oriented crystals, with few wax crystals in dendritic form. The preferred sticks of this invention thus have an essentially-uniform appearance and color, contrasted to sticks having a readily-visible axial pattern of dendritic wax crystals. In particular, in preferred processes for making the antiperspirant sticks of this invention, the compositions are cooled, immediately prior to step (c) of the process described above, to a temperature at or slightly above the temperature at which the stick composition begins to solidify, but sufficiently high so as to allow pouring of the composition into stick-form molds. In an open batch process, this point in the process is preceded by a significant increase in composition viscosity, and the batch is poured at a temperature less than about 2° C. above the temperature at which the composition fully solidifies. This preferred temperature may vary according to the particular composition employed, and can be easily determined experimentally.

The following non-limiting examples illustrate the compositions, processes and uses of the present invention.

EXAMPLE I

A stick antiperspirant composition, according to the present invention, was made with the following components:

| Components | % by weight |
|---|---|
| cyclomethicone (D-5) | 50.52 |
| REACH ® AZW-701 active[1] | 26.70 |
| stearyl alcohol | 11.35 |
| dimethicone (10 cs viscosity) | 3.00 |
| castor wax | 2.90 |
| Cab-O-Sil HS-5[2] | 0.50 |
| Microthene FN510[3] | 1.00 |
| Veecote[4] | 4.00 |
| fragrance | 0.03 |

[1]zironium-aluminum-glycine hydroxychloride complex antiperspirant active material, sold by Reheis Chemical Company.
[2]colloidal silica material, sold by Cabot Corporation, having a surface area of approximately 325 $M^2$ per gram, and a nominal particle size of 0.008 microns.
[3]low density polyethylene powder, sold by U.S.I. Chemicals, having a mean diameter of approximately 14–20 microns.
[4]anhydrous aluminum silicate powder, sold by R. T. Vanderbilt Company, Inc.

The cyclomethicone and dimethicone were mixed, the Cab-O-Sil was added, and the batch mixed. The Veecote and Microthene were added, and the batch was heated, while mixing, to about 54° C. The stearyl alcohol and castor wax were then added. The mixture was heated to about 85° C., the waxes dissolved, and the antiperspirant active was added. The mixture as cooled to approximately 78° C., and the fragrance was added, and the batch mixed. Mixing was continued and the batch cooled to approximately 50° C. and poured into stick forms. Solid antiperspirant sticks, with a uniform, random orientation of crystals, were obtained upon cooling below approximately 49° C.

An antiperspirant stick, as formulated above, was applied to the underarm of a human subject, and reduced the perspiration in the applied area. In the above example, cetyl alcohol is substituted for stearyl alcohol, with substantially similar results. Also, in the above example, dimethicone (100 cs viscosity) is substituted for dimethicone (10 cs viscosity), with substantially similar results.

EXAMPLE II

A stick antiperspirant composition, according to the present invention, is made with the following components:

| Components | % by weight |
| --- | --- |
| cyclomethicone | 46.00 |
| Macrospherical TM-95[1] | 30.50 |
| stearyl alcohol | 12.00 |
| dimethicone (350 cs) | 3.00 |
| castor wax | 3.00 |
| Syloid 244[2] | 1.50 |
| Microthene | 2.00 |
| talc | 2.00 |

[1] 5/6 basic aluminum chlorhydrate particulate antiperspirant material, sold by Reheis Chemical Company, with approximately 98% of the particles having a diameter greater than 10 microns and approximately 96% greater than 16 microns
[2] colloidal silica material, sold by Davison Chemical Division of W. R. Grace, having a surface area of approximately 310 $M^2$ per gram and a nominal particle size of 4 microns.

An antiperspirant stick is made in a manner similar to that described in Example I. The product, when applied to the underarm of a human subject, is effective as an antiperspirant.

EXAMPLE III

A stick antiperspirant composition, according to the present invention, is made with the following components:

| Components | % by weight |
| --- | --- |
| cyclomethicone (D5)* | 48.75 |
| ZAG antiperspirant active | 22.70 |
| stearyl alcohol | 12.00 |
| dimethicone (50 cs) | 3.00 |
| castor wax | 2.90 |
| Cab-O-Sil | 0.50 |
| Microthene | 1.00 |
| talc | 8.10 |
| eicosanol* | 0.25 |
| fragrance | 0.80 |

*approximate levels; the exact level of eicosanol and cyclomethicone are adjusted to yield a total eicosanol level (including amounts of eicosanol naturally present in the stearyl alcohol) of approximately 0.31% (by weight of stick), or approximately 2.5% (by total weight of fatty alcohol).

What is claimed is:

1. An antiperspirant stick composition comprising:
   (a) from about 35% to about 60% of a volatile silicone oil;
   (b) from about 1% to about 5% of a non-volatile emollient;
   (c) from about 2.5% to about 4% of a high-melting point wax;
   (d) from about 10% to about 15% of a low melting point wax;
   (e) from about 0.2% to about 1.5% of a colloidal silica material;
   (f) from about 0.5% to about 4% of an inert spherical particulate material selected from the group consisting of polyolefins, nylon, insoluble cross-linked starches, and mixtures thereof, which is comprised of essentially spherical particulates having a mean diameter of at least about 10 microns;
   (g) from about 2% to about 9% of a talcum material; and
   (h) from about 20% to about 33% of a particulate antiperspirant material;
   wherein the total level of said talcum material and said antiperspirant material is from about 25% to about 35%.

2. An antiperspirant composition, according to claim 1, wherein said antiperspirant material is present at a level of from about 25% to about 28%.

3. An antiperspirant composition, according to claim 2, wherein the combined level of said inert spherical particulate material and said talcum material is less then about 7%.

4. An antiperspirant composition according to claim 2, wherein said talcum material is present at a level of from about 2.5% to about 5.5%.

5. An antiperspirant composition, according to claim 1, wherein said total level of said talcum material and said antiperspirant material is from about 28% to about 33%.

6. An antiperspirant composition, according to claim 5, wherein said inert spherical particulate material is present at a level of from about 0.5% to about 1.5%.

7. An antiperspirant composition, according to claim 5, wherein said high melting point wax is present at a level of from about 2.5% to about 3.5%.

8. An antiperspirant composition, according to claim 7, wherein said colloidal silica material is present at a level of from about 0.4 to about 1.0%.

9. An antiperspirant composition, according to claim 8, wherein said colloidal silica material is a fumed silica having a mean particle size less than about 1 microns.

10. An antiperspirant composition, according to claim 8, wherein said low melting point wax is present at a level of from about 10.5% to about 13%.

11. An antiperspirant composition, according to claim 10, wherein said low melting point wax is selected from the group consisting of stearyl alcohol, cetyl alcohol, and mixtures thereof.

12. An antiperspirant composition, according to claim 1, wherein said non-volatile emollient is a non-volatile silicone oil.

13. An antiperspirant composition, according to claim 12, wherein said non-volatile silicone oil is present at a level of from about 2% to about 4%.

14. An antiperspirant composition according to claim 1, in stick form, comprised of a pattern of small, randomly-oriented crystals.

15. An antiperspirant composition according to claim 14, additionally comprising a long-chain fatty alcohol having at least twenty carbon atoms, at a level such that the total level of said long-chain fatty alcohols in said composition is from about 1% to about 3%, by total weight of fatty alcohols in said composition.

16. A process, for making an antiperspirant stick composition according to claim 14, comprising the steps of:
   (a) admixing said volatile silicone oil, said non-volatile emollient, said high melting point wax, said low melting point wax, said colloidal silica material, said inert spherical particulate, said talcum materials and said particulate antiperspirant material at a temperature sufficient to melt said waxes;

(b) cooling said composition to a temperature less than about 2° C. above the point at which said composition solidifies;

(c) pouring said composition into stick form molds; and (d) cooling said composition to form a solid stick composition.

* * * * *